United States Patent
Ishikubo et al.

(10) Patent No.: US 9,259,382 B2
(45) Date of Patent: Feb. 16, 2016

(54) COSMETIC COMPOSITION, HAIR COSMETIC AND HAIR TREATMENT COSMETIC

(71) Applicant: MITSUBISHI CHEMICAL CORPORATION, Chiyoda-ku (JP)

(72) Inventors: Akira Ishikubo, Mie (JP); Shoya Yoda, Mie (JP)

(73) Assignee: MITSUBISHI CHEMICAL CORPORATION, Chiyoda-ku (JP)

(*) Notice: Subject to any disclaimer, the term of this patent is extended or adjusted under 35 U.S.C. 154(b) by 159 days.

(21) Appl. No.: 13/867,517

(22) Filed: Apr. 22, 2013

(65) Prior Publication Data

US 2013/0236411 A1    Sep. 12, 2013

Related U.S. Application Data

(63) Continuation of application No. PCT/JP2011/074169, filed on Oct. 20, 2011.

(30) Foreign Application Priority Data

Oct. 22, 2010 (JP) ................. 2010-237635
Sep. 28, 2011 (JP) ................. 2011-212630

(51) Int. Cl.
| A61Q 5/12 | (2006.01) |
| A61K 8/81 | (2006.01) |
| C08F 220/28 | (2006.01) |
| A61K 8/34 | (2006.01) |
| A61K 8/41 | (2006.01) |
| A61Q 5/00 | (2006.01) |
| A61K 8/891 | (2006.01) |

(52) U.S. Cl.
CPC ............... *A61K 8/8152* (2013.01); *A61K 8/342* (2013.01); *A61K 8/416* (2013.01); *A61K 8/8135* (2013.01); *A61K 8/891* (2013.01); *A61Q 5/00* (2013.01); *A61Q 5/12* (2013.01); *C08F 220/28* (2013.01)

(58) Field of Classification Search
CPC . A01N 59/12; A01N 2300/00; A01N 25/004; A01N 25/10; A61Q 5/06; A61Q 5/12; A61Q 5/00; A61Q 5/02; A61Q 19/00; A61Q 15/00; A61Q 19/10; A61Q 1/02; A61Q 17/005; A61Q 5/065; A61Q 5/10
See application file for complete search history.

(56) References Cited

U.S. PATENT DOCUMENTS

| 8,003,088 B2 | 8/2011 | Yoda et al. |
| 8,158,115 B2 | 4/2012 | Yoda et al. |
| 2008/0286218 A1 | 11/2008 | Giroud et al. |
| 2010/0105592 A1 | 4/2010 | Yoda et al. |
| 2011/0256086 A1 | 10/2011 | Yoda et al. |

FOREIGN PATENT DOCUMENTS

| CN | 101193927 A | 6/2008 | |
| EP | 1 911 778 A1 | 4/2008 | |
| FR | 2 872 423 | 1/2006 | |
| JP | 8-283145 A | 10/1996 | |
| JP | 2001-011491 A | 1/2001 | |
| JP | 2004-018414 | 1/2004 | |
| JP | 2005-002207 A | 1/2005 | |
| JP | 2008-182814 | 7/2006 | |
| JP | 2006-257188 | 9/2006 | |
| JP | 2007-137830 | 6/2007 | |
| JP | 2007-161986 | 6/2007 | |
| JP | 2009-161520 A | 7/2009 | |
| JP | 2009-172503 A | 8/2009 | |
| JP | 2009-185304 A | 8/2009 | |
| JP | 2012-031409 A | 2/2012 | |
| WO | 2005/072685 | 8/2005 | |
| WO | WO2005/072685 | * 8/2005 | ................ 424/401 |
| WO | WO 2005/072685 A1 | 8/2005 | |

OTHER PUBLICATIONS

Office Action issued on Jun. 4, 2014 in the corresponding Chinese Patent Application No. 201180050888.4 (with English Translation).
Japanese Office Action issued Dec. 16, 2014 in Patent Application No. 2011-212630 (with English Translation).
Office Action issued Feb. 5, 2015 in Chinese Patent Application No. 201180050888.4 (with English language translation).
Mexican Office Action issued May 27, 2015 in Patent Application No. MX/a/2013/004519 (with English Translation).
Chinese Office Action issued Jul. 9, 2015 in Patent Application No. 201180050888.4.
International Search Report issued Jan. 24, 2012 in PCT/JP2011/074169 filed Oct. 20, 2011.
Office Action issued on Aug. 18, 2015 in the corresponding Japanese Patent Application No. 2011-212630 (with English Translation).
Supplementary European Search Report issued Oct. 28, 2015, in European Patent Application No. 11834437.3 filed Oct. 20, 2011.
Office Action issued Nov. 11, 2015, in Mexican Patent Application No. MX/a/2013/004519 filed Oct. 20, 2011 (with English translation).

* cited by examiner

*Primary Examiner* — Audrea Buckley
(74) *Attorney, Agent, or Firm* — Oblon, McClelland, Maier & Neustadt, L.L.P.

(57) ABSTRACT

The present invention relates to a cosmetic composition comprising: a copolymer having a constituent unit corresponding to (A) a vinyl monomer having a carboxyl group in a structure and a constituent unit corresponding to (B) a vinyl monomer represented by the following formula (1); a cationic surfactant; a higher alcohol; and a silicone oil:

$$CH_2=C(R^1)-CO-X-(Q-O)_r-R^2 \qquad (1)$$

wherein $R^1$ is a hydrogen atom or a methyl group; $R^2$ is a hydrogen atom or an alkyl group having a carbon number of 1 to 5, each of which may have a substituent; Q is an alkylene group having a carbon number of 2 to 4, which may have a substituent; r represents an integer of 2 to 15; and X represents an oxygen atom or NH, and the number of atoms bonded linearly to each other in the structure of $-(Q-O)_r-R^2$ is 70 or less.

11 Claims, No Drawings

COSMETIC COMPOSITION, HAIR COSMETIC AND HAIR TREATMENT COSMETIC

TECHNICAL FIELD

The present invention relates to a cosmetic composition, a hair cosmetic and a hair treatment cosmetic, each of which contains a copolymer exceptionally effective in enhancing the hair conditioning effect.

BACKGROUND ART

In recent years, as the booming market of damage control products such as high-grade shampoo, rinse and out-bath treatment shows, consumer awareness of damage to hair of head is increasing. For reducing the damaged feel (enhancing the touch feel) of hair, a rinse (conditioner) is used after washing the hair of head with a shampoo, and when the damaged feel still remains, a treatment that is applied in a bathroom or a treatment that is applied outside of a bathroom and not washed out, is used.

The damaged feel of hair is expressed mainly by sensory evaluation of, for example, a friction between hairs or between hair and hand or a parched look or hardness due to lack of moisture. With an attempt to suppress the damaged feel, in a rinse or a treatment, a cationic surfactant such as stearyltrimethylammonium chloride is blended as a component for reducing the friction and softening the hair (softener component).

On the other hand, for reducing the damaged feel of hair, it has been heretofore attempted, for example, to design the surfactant structure, blend a silicone oil or blend a resin. As to the addition of a resin, for example, a cosmetic preparation having blended therein a copolymer having an anionic group-containing unit and a silicon atom-containing unit or a resin compound having an anionic group and a silicon atom per molecule is supposed to be capable of imparting elasticity to the hair and producing an excellent conditioning effect such as flexibility and smoothness (for example, Patent Document 1). A cosmetic preparation having blended therein a resin compound containing an anionic vinyl monomer and a hydroxyl group-containing nonionic vinyl monomer is also supposed to increase the conditioning performance (for example, Patent Documents 2 and 3).

BACKGROUND ART DOCUMENT

Patent Document

Patent Document 1: JP-A-2004-018414
Patent Document 2: JP-A-2007-161986
Patent Document 3: JP-A-2007-137830

SUMMARY OF INVENTION

Problem that Invention is to Solve

The rinse or treatment requiring washing-off must be rinsed after application to hair, but according to studies by the present inventors, there has been found a problem that most of the softener component blended flows out during rinsing.

Furthermore, a higher conditioning effect is recently demanded. For example, when a shampoo and rinse treatment can produce a high treatment effect without using many treatments, the burden in terms of cost on the consumer can be lessened. For this reason, demands for such improvement on a hair cosmetic are increasing.

An object of the present invention is to solve those problems and provide a copolymer capable of realizing a hair cosmetic ensuring that a softener component such as cationic surfactant can persist on hair even after water rinsing without impairing the feel such as smoothness in use and an excellent conditioning effect can be produced without impairing the feel such as smoothness in use, and a cosmetic composition and a hair cosmetic each containing the copolymer.

Means for Solving Problem

As described above, there has been found a problem that a rinse needs to be water-rinsed after application to hair and most of the softener component flows out during rinsing. The present inventors have made intensive studies based on the expectation that when most of a softener component such as cationic surfactant can be caused to remain on hair even after rinsing, the conditioning property may be enhanced. As a result, it has been found that a copolymer having a constituent unit corresponding to a carboxyl group-containing vinyl monomer and a constituent unit corresponding to a hydrophilic nonionic vinyl monomer of a specific structure, and containing the constituent unit corresponding to a carboxyl group-containing vinyl monomer in a specific ratio, assists a softener component to exhibit persistence on hair and give a high conditioning effect without impairing the feel such as smoothness in use. The present invention has been accomplished based on this finding.

That is, the gist of the present invention resides in the following [1] to [12].

[1] A cosmetic composition, comprising:
a copolymer having a constituent unit corresponding to (A) a vinyl monomer having a carboxyl group in a structure and a constituent unit corresponding to (B) a vinyl monomer represented by the following formula (1);
a cationic surfactant;
a higher alcohol; and
a silicone oil:

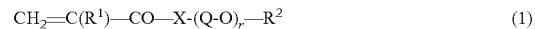

(in formula (1), $R^1$ represents a hydrogen atom or a methyl group; $R^2$ represents a hydrogen atom or an alkyl group having a carbon number of 1 to 5, each of which may have a substituent; Q represents an alkylene group having a carbon number of 2 to 4, which may have a substituent; r represents an integer of 2 to 15; and X represents an oxygen atom or NH, provided that in formula (1), the number of atoms bonded linearly to each other in the structure of -(Q-O)$_r$—$R^2$ is 70 or less).

[2] The cosmetic composition as described in [1] above, wherein a proportion of the constituent unit corresponding to the vinyl monomer (A) is from 15 to 60 mass % based on the total mass of the copolymer.

[3] The cosmetic composition as described in [1] or [2] above, wherein a proportion of the constituent unit corresponding to the vinyl monomer (B) is from 40 to 85 mass % based on the total mass of the copolymer.

[4] The cosmetic composition as described in any one of [1] to [3] above, wherein the vinyl monomer (A) is represented by the following formula (2) or (3):

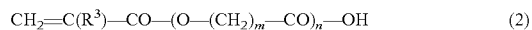

(in formula (2), $R^3$ represents a hydrogen atom or a methyl group; m represents an integer of 1 to 4; and n represents an integer of 0 to 4):

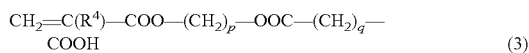

$$CH_2\!=\!C(R^4)\!-\!COO\!-\!(CH_2)_p\!-\!OOC\!-\!(CH_2)_q\!-\!COOH \quad (3)$$

(in formula (3), $R^4$ represents a hydrogen atom or a methyl group; and each of p and q independently represents an integer of 2 to 6).

[5] The cosmetic composition as described in any one of [1] to [4] above,
wherein a weight average molecular weight is from 3,000 to 2,000,000.

[6] The cosmetic composition as described in any one of [1] to [5] above, which further comprises:
a constituent unit corresponding to (C) a vinyl monomer having an alkyl group with a carbon number of 12 to 22 in an amount of 40 mass % or less based on the total mass of the copolymer.

[7] The cosmetic composition as described in any one of [1] to [6] above, which comprises:
from 0.1 to 5 mass % of the copolymer; and
from 55 to 99.6 mass % of water.

[8] The cosmetic composition as described in any one of [1] to [7] above, which comprises:
from 0.1 to 20 mass % of the cationic surfactant.

[9] The cosmetic composition as described in any one of [1] to [8] above, which comprises:
from 0.1 to 20 mass % of the higher alcohol.

[10] The cosmetic composition as described in any one of [1] to [9] above, which comprises:
from 0.1 to 10 mass % of the silicone oil,

[11] A hair cosmetic, comprising:
the cosmetic composition as described in any one of [1] to [10] above.

[12] A hair treatment cosmetic, comprising:
the cosmetic composition as described in any one of [1] to [10] above.

Effects of Invention

The copolymer for use in the present invention has an excellent adsorption effect of a cationic surfactant and when used as a cosmetic composition, exerts an excellent performance in terms of viscosity and smoothness upon application. Accordingly, in the case where the copolymer is blended in a rinse or the like, the role of a cationic surfactant as a softener can be sustained for a long time even after water rinsing without impairing the feel such as smoothness in use, and a hair cosmetic having an excellent conditioning effect can be produced.

MODE FOR CARRYING OUT INVENTION

The mode for carrying out the present invention is described in detail below, but the constituent requirements described below are representative examples of the embodiment of the present invention, and the present invention is not limited to these contents.

Incidentally, the expression "(meth)acrylic acid" as used in the description of the present invention is intended to embrace both acrylic acid and methacrylic acid. Also, the expression "(numerical or physical value) to (numerical or physical value)" as used in the description of the invention is intended to include the numerical or physical values before and after "to".

Also, the "smoothness upon application" as used in the present invention indicates an evaluation described in Examples later and even if the adsorption amount of a cationic surfactant or the viscosity of a cosmetic composition is excellent, when the smoothness upon application is inferior to the "reference standard product", the effect is regarded to be poor.

Furthermore, in the description of the present invention, "mass %", "ppm by mass" and "parts by mass" have the same meanings as "wt %", "ppm by weight" and "parts by weight", respectively.

1. Copolymer

The copolymer contained in the cosmetic composition of the present invention is characterized by being a copolymer having a constituent unit corresponding to (A) a vinyl monomer having a carboxyl group in the structure and a constituent unit corresponding to (B) a vinyl monomer represented by the following formula (1):

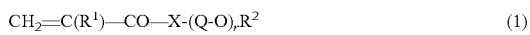

$$CH_2\!=\!C(R^1)\!-\!CO\!-\!X\text{-}(Q\text{-}O)_r R^2 \quad (1)$$

(in formula (1), $R^1$ is a hydrogen atom or a methyl group, $R^2$ is a hydrogen atom or an alkyl group having a carbon number of 1 to 5, each of which may have a substituent, Q is an alkylene group having a carbon number of 2 to 4, which may have a substituent, r is an integer of 2 to 15, and X is an oxygen atom or NH, provided that in formula (1), the number of atoms bonded linearly to each other in the structure of -(Q-O)$_r$—$R^2$ is 70 or less).

<Constituent Unit Corresponding to Vinyl Monomer (A)>

The copolymer for use in the present invention has a constituent unit corresponding to (A) a vinyl monomer having a carboxyl group in the structure and at the same time, the proportion of the constituent unit corresponding to the vinyl monomer (A) is preferably from 15 to 60 mass % based on the total mass of the copolymer.

The reason why the copolymer for use in the present invention preferably contains a constituent unit corresponding to (A) a vinyl monomer having a carboxyl group in the structure in a specific proportion is as follows.

One object of the present invention is to increase the adsorption amount of a cationic surfactant when the copolymer and the cationic surfactant are used together. In the present invention, the copolymer is designed to increase the adsorption amount to a cationic surfactant, and the main factor in the presumed mechanism thereof includes the following two points:

1) strong interaction of the copolymer with the cationic surfactant: thanks to polarization of oxygen of —OH of a carboxyl group in the copolymer, the interaction between the copolymer and the cationic surfactant is increased; and 2) strong interaction of a composite of the copolymer and the cationic surfactant with hair: the interaction of polarized hydrogens of a cationic group of the cationic surfactant and a carboxyl group of the copolymer with the hair surface (anion) is increased.

According to the studies by the present inventors, it has been found that when the proportion of the constituent unit corresponding to the vinyl monomer (A) is set to be from 15 to 60 mass % based on the total mass of the copolymer, the presumed mechanisms 1) and 2) produce a highest effect. The proportion of the constituent unit corresponding to the vinyl monomer (A) based on the total mass of the copolymer is preferably 20 mass % or more, more preferably 25 mass % or more, and on the other hand, preferably 55 mass % or less, more preferably 50 mass % or less, still more preferably 45 mass % or less, and most preferably 40 mass % or less. When the proportion of the constituent unit corresponding to the vinyl monomer (A) in the copolymer is large, the adsorptivity of the cationic surfactant is enhanced, but if the proportion is excessively large, the smoothness upon application or the viscosity may be impaired.

The copolymer may contain only one kind of a constituent unit corresponding to the vinyl monomer (A) or may contain two or more kinds of constituent units corresponding to the vinyl monomer (A).

As described above, in the present invention, the technical significance of the constituent unit corresponding to the vinyl monomer (A) resides in that the constituent unit corresponding to the vinyl monomer (A) has a carboxyl group for bringing about an interaction between the cationic surfactant and the hair surface. Accordingly, the constituent unit corresponding to the vinyl monomer (A) is not particularly limited in its kind as long as the constituent unit has a carboxyl group. Specific examples thereof include an unsaturated carboxylic acid monomer having a carbon number of 3 to 22, typified by the later-described compound represented by formula (2) or (3), such as (meth)acrylic acid, crotonic acid, maleic acid, fumaric acid, itaconic acid, angelic acid, tiglic acid, acryloyloxyethyl succinate, 2-methacryloyloxyethyl succinate and acrylic acid 2-carboxyethyl acrylate oligomer. The unsaturated carboxylic acid monomer preferably has a carbon number of 4 or more and on the other hand, preferably has a carbon number of 20 or less, more preferably a carbon number of 18 or less, still more preferably a carbon number of 10 or less, yet still more preferably a carbon number of 6 or less. Also, the number of carboxyl groups in the constituent unit corresponding to the vinyl monomer (A) is preferably from 1 to 4, more preferably from 1 to 3, still more preferably 1 to 2, and most preferably 1.

In order to increase the adsorption effect to the cationic surfactant, the vinyl monomer (A) is preferably an unsaturated carboxylic acid monomer represented by the following formula (2) or (3):

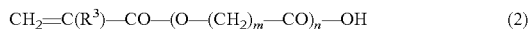

(in formula (2), $R^3$ represents a hydrogen atom or a methyl group, m represents an integer of 1 to 4, and n represents an integer of 0 to 4);

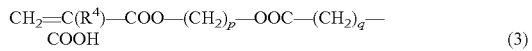

(in formula (3), $R^4$ represents a hydrogen atom or a methyl group, and each of p and q independently represents an integer of 2 to 6).

In formula (2), $R^3$ is preferably a hydrogen atom. m is preferably from 2 to 3. n is preferably from 0 to 2 and most preferably 0.

Specific examples of the monomer represented by formula (2) include a (meth)acrylic acid, a crotonic acid, a maleic acid, a fumaric acid, an itaconic acid, an angelic acid, a tiglic acid, and a 2-carboxyethyl acrylate oligomer. Among these, an acrylic acid and a methacrylic acid are preferred, and an acrylic acid is most preferred.

In formula (3), $R^4$ is preferably a hydrogen atom, p is preferably from 2 to 3, and q is preferably from 2 to 3.

Specific examples of the monomer represented by formula (3) include acryloyloxyethyl succinate and 2-methacryloyloxyethyl succinate.

Incidentally, the copolymer may be a copolymer containing, as the constituent unit corresponding to the vinyl monomer (A), only a constituent unit corresponding to the vinyl monomer represented by formula (2), may be a copolymer containing only a constituent unit corresponding to the vinyl monomer represented by formula (3), or may be a copolymer containing a constituent unit corresponding to the vinyl monomer represented by formula (2) and a constituent unit corresponding to the vinyl monomer represented by formula (3).

<Constituent Unit Corresponding to Vinyl Monomer (B)>

The copolymer has a constituent unit corresponding to (B) a vinyl monomer represented by the following formula (1):

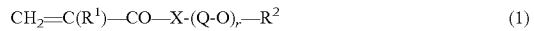

(in formula (1), $R^1$ represents a hydrogen atom or a methyl group, $R^2$ represents a hydrogen atom or an alkyl group having a carbon number of 1 to 5, each of which may have a substituent, Q represents an alkylene group having a carbon number of 2 to 4, which may have a substituent, r represents an integer of 2 to 15, and X represents an oxygen atom or NH, provided that in formula (1), the number of atoms bonded linearly to each other in the structure of $-(Q-O)_r-R^2$ is 70 or less).

In formula (1), $R^1$ is a hydrogen atom or a methyl group.

$R^2$ is a hydrogen atom or an alkyl group having a carbon number of 1 to 5, each of which may have a substituent. In the case where $R^2$ has a substituent, the substituent indicates a substituent incapable of reacting with other moieties in the copolymer. The vinyl monomer (B) preferably has hydrophilicity and therefore, $R^2$ is preferably a hydrogen atom or an alkyl group having a carbon number of 1 to 3, more preferably a hydrogen atom or an alkyl group having a carbon number of 1 or 2.

X is an oxygen atom or NH. X is preferably an oxygen atom.

Q is an alkylene group having a carbon number of 2 to 4, preferably a carbon number of 2 to 3, which may have a substituent. In the case where the alkylene group of Q has a substituent, the substituent indicates a substituent incapable of reacting with other moieties in the copolymer. If the volume occupied by the substituent is too large, the volume occupied by the substituent in the structure moiety of $X-(Q-O)_r-R^2$ of the vinyl monomer (B) becomes large, as a result, when a rinse lamella is formed, the interaction between the rinse lamella and a carboxyl group of the vinyl monomer (A) may be weakened and the adsorptivity of the cationic surfactant may be reduced. Therefore, the substituent is a substituent having a molecular weight of 50 or less, and specific examples thereof include a hydroxyl group, a methoxy group, and an ethoxy group. However, Q is more preferably an alkylene group having no substituent. Also, the substituent of the alkylene group of Q is preferably smaller in the molecular weight than the structure moiety of $-(Q-O)_r-$.

r is an integer of 2 to 15. r is preferably 3 or more and, on the other hand, preferably 12 or less.

However, in the copolymer, the length of the side chain moiety (the structural moiety $X-(Q-O)_r-R^2$ in formula (1)) of the constituent unit corresponding to the vinyl monomer (B) greatly affects the smoothness upon application or the effect on the adsorption amount of the cationic surfactant when the copolymer is used as a cosmetic composition, and for this reason, the number of atoms linearly bonded to each other in the structure of $-(Q-O)_r-R^2$ in formula (1) is 70 or less. Accordingly, for example, in the case where Q is an n-butylene group, r=15 and $R^2$ is an n-pentyl group, the number of atoms linearly bonded to each other in the structure of $-(Q-O)_r-R^2$ becomes 80 and therefore, this falls outside the definition of formula (1). The number of atoms linearly bonded to each other in the structure of $-(Q-O)_r-R^2$ in formula (1) is preferably 60 or less, more preferably 40 or less, still more preferably 28 or less, yet still more preferably 20 or less, As described in the constituent unit corresponding to the vinyl copolymer (A), when a given amount or more of a COOH group is incorporated into the copolymer, the adsorptivity of the cationic surfactant is enhanced, but there arises a problem that when blended in a hair cosmetic such as rinse and treatment, the smoothness upon application or the viscosity is impaired. This is presumed to be a phenomenon caused by provoking a strong interaction between a copolymer present in a hydrophilic layer of a cationic surfactant-higher alcohol aggregate (rinse lamella) and a cationic group-containing layer to compress the hydrophilic layer (when the interaction is particularly strong, leading to collapse), and in turn, bringing about reduction in the flexibility of lamella or deterioration of the continuity of lamella.

As a result of intensive studies, the present inventors have found that by incorporating a constituent unit corresponding to a hydrophilic nonionic monomer having a given length or more in the side chain into the copolymer, the compression•collapse of the rinse lamella layer can be prevented from occurring. On the other hand, it has been revealed that if the length of the side chain is too long, although the smoothness upon application can be maintained, the adsorption amount of the cationic surfactant is reduced, and thus, a specific length as the side chain of the hydrophilic monomer is required in order to achieve the smooth feel upon application and the high adsorptivity of the cationic surfactant. According to the studies by the present inventors, it has been found that when r in formula (1) determining the side chain length of the constituent unit corresponding to the vinyl monomer (B) is from 2 to 15, both the smoothness upon application and the adsorptivity of the cationic surfactant can be satisfied. For this reason, r in formula (1) representing the vinyl monomer (B) is from 2 to 15 and is preferably 3 or more and on the other hand, preferably 12 or less.

Examples of the vinyl monomer (B) include a methoxypolyethylene glycol(meth)acrylate (the number of polyethylene glycol repeating units (r in formula (1)) is from 2 to 15), a polyethylene glycol(meth)acrylate (the number of polyethylene glycol repeating units (r in formula (1)) is from 2 to 15), a methoxypolyethylene glycol/polypropylene glycol(meth)acrylate (the number of polyethylene glycol/polypropylene glycol repeating units (r in formula (1)) is from 2 to 15), a polyethylene glycol/polypropylene glycol(meth)acrylate (the number of polyethylene glycol/polypropylene glycol repeating units (r in formula (1)) is from 2 to 15), a methoxypolyethylene glycol/polybutylene glycol(meth)acrylate (the number of polyethylene glycol/polybutylene glycol repeating units (r in formula (1)) is from 2 to 15), a polyethylene glycol/polybutylene glycol(meth)acrylate (the number of polyethylene glycol/polybutylene glycol repeating units (r in formula (1)) is from 2 to 15), a methoxypolyethylene glycol (meth)acrylamide (the number of polyethylene glycol repeating units (r in formula (1)) is from 2 to 15), and a polyethylene glycol(meth)acrylamide (the number of polyethylene glycol repeating units (r in formula (1)) is from 2 to 15). Among these, preferred are a methoxypolyethylene glycol(meth)acrylate (the number of polyethylene glycol repeating units (r in formula (1)) is from 3 to 12), a polyethylene glycol(meth)acrylate (the number of polyethylene glycol repeating units (r in formula (1)) is from 3 to 12), a methoxypolyethylene glycol/polypropylene glycol(meth)acrylate (the number of polyethylene glycol/polypropylene glycol repeating units (r in formula (1)) is from 3 to 12), a polyethylene glycol/polypropylene glycol(meth)acrylate (the number of polyethylene glycol/polypropylene glycol repeating units (r in formula (1)) is from 3 to 12), a methoxypolyethylene glycol/polybutylene glycol(meth)acrylate (the number of polyethylene glycol/polybutylene glycol repeating units (r in formula (1)) is from 3 to 12), and a polyethylene glycol/polybutylene glycol(meth)acrylate (the number of polyethylene glycol/polybutylene glycol repeating units (r in formula (1)) is from 3 to 12); and more preferred are a methoxypolyethylene glycol(meth)acrylate (the number of polyethylene glycol repeating units (r in formula (1)) is from 3 to 12) and a polyethylene glycol(meth)acrylate (the number of polyethylene glycol repeating units (r in formula (1)) is from 3 to 12).

The copolymer may contain only one kind of a constituent unit corresponding to the vinyl monomer (B) or may contain two or more kinds of constituent units corresponding to the vinyl monomer (B).

In the copolymer, the proportion of the constituent unit corresponding to the vinyl monomer (B) is preferably 40 to 85 mass % based on the total mass of the copolymer. When the proportion of the constituent unit corresponding to the vinyl monomer (B) is 40 mass % or more, the effect of enhancing the smoothness or feel upon application, which is attained by allowing a constituent unit corresponding to the vinyl monomer (B) to be present in the copolymer, can be satisfactorily produced, and when the proportion is 85 mass % or less, the proportion of the constituent unit corresponding to the vinyl monomer (A) in the copolymer can be secured and in turn, the adsorptivity of the cationic surfactant can be increased. The proportion of the constituent unit corresponding to the vinyl monomer (B) in the copolymer is more preferably 45 mass % or more, still more preferably 50 mass % or more, and on the other hand, more preferably 80 mass % or less, still more preferably 75 mass % or less.

<Constituent Unit Corresponding to Vinyl Monomer (C)>

In view of conditioning effects such as smoothness upon application, the copolymer preferably contains, as the constituent unit, a constituent unit corresponding to (C) a vinyl monomer having an alkyl group with a carbon number of 12 to 22 in an amount of 40 mass % or less based on the total mass of said copolymer, in addition to the constituent units corresponding to the vinyl monomers (A) and (B) above. The content of the constituent unit corresponding to the vinyl monomer (C) is more preferably 30 mass % or less, still more preferably 25 mass % or less, for example, from 0 to 20 mass %.

The reason why the conditioning effects such as smoothness upon application are improved when the copolymer contains a constituent unit corresponding to the vinyl monomer (C) is considered to be because an alkyl group having a carbon number of 12 to 22 as the hydrophobic group in the side chain of the vinyl monomer (C) intrudes into the hydrophobic layer of a rinse lamella and the fluidity of the lamella is thereby enhanced. However, if the content of the constituent unit corresponding to the vinyl monomer (C) in the copolymer is too large, this tends to cause collapse of the lamella structure and impair the spread upon application.

As the vinyl monomer (C), a (meth)acrylate monomer having an alkyl group with a carbon number of 12 to 22 is preferably used, because the fluidity of the hydrophobic phase in the rinse lamella structure put into contact with hair is increased to produce good effects such as smoothness upon application. Among others, a vinyl monomer having a branched alkyl group is preferred.

Examples of the (meth)acrylate monomer having an alkyl group with a carbon number of 12 to 22 include a myristyl (meth)acrylate, an isostearyl(meth)acrylate, a stearyl(meth) acrylate, a behenyl(meth)acrylate, a cetyl(meth)acrylate, a lauryl(meth)acrylate, and a synthetic lauryl(meth)acrylate (here, the "synthetic lauryl(meth)acrylate" means an alkyl (meth)acrylate where an alkyl group having a carbon number of 12 and an alkyl group having a carbon number of 13 are mixed). Among others, a (meth)acrylate monomer having an alkyl group with a carbon number of 12 to 20 is preferred, and a (meth)acrylate monomer having an alkyl group with a carbon number of 16 to 18 is more preferred.

The copolymer may contain only one kind of a constituent unit corresponding to the vinyl monomer (C) or may contain two or more kinds of constituent units corresponding to the vinyl monomer (C).

<Constituent Units Corresponding to Other Monomers>

In addition to the vinyl monomers (A), (B) and (C), the copolymer may further contain structural units corresponding to other vinyl-based monomers as long as the effects of the present invention are not impaired. Other vinyl-based monomers which can be used include, for example, a nonionic monomer, an amphoteric monomer, a semipolar monomer, a cationic monomer, and a polysiloxane group-containing monomer. However, the other monomers exclude the vinyl monomers (A), (B) and (C) above.

The content of the structural unit derived from other monomers in the copolymer may be appropriately determined without deviating from the purport of the present invention. For example, the content may be appropriately determined in the range where the affinity of the copolymer for skin or hair and when used for a hair cosmetic, the conditioning effect and the like are not inhibited, and the content is usually 40 mass % or less, preferably 30 mass % or less, more preferably 20 mass % or less, still more preferably 10 mass % or less, based on the total mass of the copolymer.

However, if a cationic functional group is present in the copolymer, this may impede complex formation with the above-descried cationic surfactant. Therefore, the proportion of the cationic functional group in the copolymer is preferably small and, for example, is preferably 10 mol % or less based on all functional groups in the copolymer, and it is more preferred to contain substantially no cationic functional group.

Examples of other monomers are set forth below, but the copolymer may contain a constituent unit corresponding to a monomer other than those recited below. Also, only one kind of a constituent unit corresponding to other monomers may be contained in the copolymer, or two or more of the same kind or different kinds of constituent units corresponding to other monomers may be contained.

Examples of the nonionic monomer include an ester of an alcohol having a carbon number of 1 to 22 and a (meth)acrylic acid, an amide of an alkylamide having a carbon number of 1 to 22 and a (meth)acrylic acid, a monoester of ethylene glycol, 1,3-propylene glycol or the like and a (meth)acrylic acid, an ester where a hydroxyl group of the monoester above is etherified with methanol, ethanol or the like, and a (meth)acroylmorpholine.

Examples of the amphoteric monomer include a betaine group-containing (meth)acryl ester and a betaine group-containing (meth)acrylamide.

Examples of the semipolar monomer include an amine oxide group-containing (meth)acrylic acid ester and an amine oxide group-containing (meth)acrylamide.

Examples of the cationic monomer include a quaternary ammonium group-containing (meth)acrylic acid ester and a quaternary ammonium group-containing (meth)acrylamide.

The polysiloxane group-containing monomer is a compound having a polysiloxane structure and a structure capable of connecting to the copolymer by covalent bonding. Such a constituent unit is considered to exhibit high affinity for a silicone oil usually used in combination in a cosmetic composition and serve to connect the other constituent unit in the copolymer to a silicone oil and thereby increase the adsorption force of the silicone oil to skin, hair, particularly damaged hair, or the like. However, in order not to impair the effects of the copolymer, in the case of using the polysiloxane group-containing monomer as a copolymerization component, the proportion thereof in the copolymer is set to 40 mass % or less, preferably 30 mass % or less, more preferably 20 mass % or less.

The polysiloxane structure is a structure where two or more repeating structural units represented by the following formula (4) are connected:

$$-(SiR^5R^6-O)-\qquad(4)$$

(in formula (4), each of $R^5$ and $R^6$ independently represents an alkyl group having a carbon number of 1 to 3 or a phenyl group).

Examples of the structure which can be connected with the copolymer by covalent bonding include, but are not limited to, a structure having a vinyl structure such as (meth)acrylic ester and (meth)acrylamide and being copolymerizable with other monomers, a structure having a functional group such as thiol and being capable of connecting with the copolymer by chain transfer during polymerization, and a structure having an isocyanate group, a carboxylic acid group, a hydroxyl group, an amino group or the like and being capable of reacting and connecting with a functional group of the copolymer.

A plurality of these connectable structures may be contained in one polysiloxane group-containing monomer. In the copolymer, the polysiloxane structure may be connected with the main chain by a graft structure, or conversely, the polysiloxane structure may serve as the main chain and another structure may be connected therewith by a graft structure. The polysiloxane structure and another structure may be also linearly connected by a block structure.

Among others, the polysiloxane group-containing monomer is preferably a monomer represented by the following formula (5):

$$CH_2=C(R^7)-Z-(SiR^8R^9-O)_s-R^{10}\qquad(5)$$

(wherein $R^7$ represents a hydrogen atom or a methyl group, each of $R^8$ and $R^9$ independently represents an alkyl group having a carbon number of 1 to 3 or a phenyl group, $R^{10}$ represents an alkyl group having a carbon number of 1 to 8, Z represents a divalent linking group or a direct bond, and s represents an integer of 2 to 200), A monomer where s is 3 or more is more preferred, and a monomer where s is 5 or more is still more preferred. As the integer s is larger, the affinity for a silicone oil is enhanced. Also, s is more preferably 50 or less. As the integer s is smaller, the copolymerizability with other monomers is increased.

Z represents a divalent linking group or a direct bond and is preferably a linking group composed of one member or the combination of two or more members of the structures described below. The number of structures combined is not limited but is usually 5 or less. Also, the direction in which the following structure faces (which end is on the polysiloxane group side) is arbitrary. In the followings, R represents an alkylene group having a carbon number of 1 to 6 or a phenylene group.

—COO—R—
—CONH—R—
—O—R—
—R—

The polysiloxane group-containing monomer represented by formula (5) is not particularly limited as long as it is included in the formula, but examples thereof include α-(vinylphenyl)polydimethylsiloxane, α-(vinylbenzyloxypropyl)polydimethylsiloxane, α-(vinylbenzyl)polymethylphenylsiloxane, α-(methacryloyloxypropyl)polydimethylsiloxane, α-(methacryloyloxypropyl)polymethylphenylsiloxane, and α-(methacryloylaminopropyl)polydimethylsiloxane. As for the polysiloxane group-containing monomer, one kind of a monomer may be used alone, or two or more kinds of monomers may be used in combination, As such a polysiloxane group-containing monomer, a commercially available product may be also used. For example, as the α-(methacryloyloxypropyl)polydimethylsiloxane, SILAPLANE (produced by Chisso Corp.) is available, and examples thereof include SILAPLANE FM0711 (molecular weight: 1,000), SILAPLANE FM0721 (molecular weight: 5,000), and SILAPLANE FM0722 (molecular weight: 10,000).

In the copolymer for use in the present invention, a crosslinking agent such as polyfunctional acrylate may be introduced so as to adjust the molecular weight or viscosity of the copolymer, but, as described later, it is preferred not to contain a crosslinking agent.

<Structural Analysis>

The contents of respective constituent units corresponding to the vinyl monomers (A), (B) and (C) and other monomers in the copolymer can be measured by IR absorption or Raman scattering of various functional groups or carbon skeletons, such as carbonyl group, amide bond and polysiloxane structure, or by various NMR measurements typified, for example, by $^1$H-NMR or $^{13}$C-NMR of a methyl group, an amide bond moiety, a methyl or methylene group adjacent thereto, or the like of polydimethylsiloxane.

<Weight Average Molecular Weight>

The weight average molecular weight of the copolymer for use in the present invention is preferably from 3,000 to 2,000,000. When the weight average molecular weight is 3,000 or more, the conditioning effect by adsorption of a complex with the cationic surfactant to hair or skin is more increased. The weight average molecular weight of the copolymer is more preferably 5,000 or more, still more preferably 10,000 or more, and on the other hand, when the weight average molecular weight is 2,000,000 or less, the feel after drying can be more improved. The weight average molecular weight of the copolymer is more preferably 1,000,000 or less, still more preferably 500,000 or less, yet still more preferably 100,000 or less, and most preferably 50,000 or less.

The molecular weight of the copolymer can be adjusted, for example, by controlling the polymerization degree of the copolymer. Furthermore, the molecular weight can be also controlled by increasing or decreasing the amount added of a crosslinking agent such as polyfunctional acrylate. However, excess addition of a crosslinking agent, even if only a little, makes it difficult to control the industrial production, for example, by causing rapid increase in the molecular weight and the viscosity. Therefore, it is most preferred not to contain a crosslinking agent.

The weight average molecular weight of the copolymer can be measured by gel permeation chromatography (GPC). The developing solvent used for the gel permeation chromatography is not particularly limited as long as it is a solvent usually used, but the weight average molecular weight can be measured using a mixed solvent of water/methanol/acetic acid/sodium acetate described in Examples later.

<Viscosity>

In the present invention, the copolymer preferably has a viscosity of 5 to 20,000 mPa·s at 25° C. as a 20 mass % ethanol solution. The viscosity is more preferably 10 mPa·s or more, still more preferably 15 mPa·s or more, and on the other band, more preferably 10,000 mPa·s or less, still more preferably 5,000 mPa·s or less. When the viscosity of the copolymer is from 5 to 20,000 mPa·s, this is preferred in view of handling. The viscosity can be measured using a B-type viscometer or the like.

Similarly to the weight average molecular weight, the viscosity of the copolymer can be adjusted, for example, by controlling the polymerization degree of the copolymer or can be controlled by increasing or decreasing the amount added of a crosslinking agent such as polyfunctional acrylate.

<Adsorption Amount of Cationic Surfactant>

The adsorption amount of the cationic surfactant at the time of treating hair with a cosmetic composition having blended therein the copolymer, particularly with a hair cosmetic such as rinse and treatment, may vary depending on the blending amount of the cationic surfactant in the hair cosmetic, but, for example, when the blending amount of the cationic surfactant is 1.5 mass %, the adsorption amount of the cationic surfactant to the copolymer is preferably from 50 to 3,000 ppm by mass. Thanks to the adsorption amount of the cationic surfactant of 50 ppm by mass or more, the conditioning effect is more increased. The adsorption amount is more preferably 75 ppm by mass or more, still more preferably 100 ppm by mass or more, and on the other hand, thanks to the adsorption amount of the cationic surfactant of 3,000 ppm by mass or less, the feel after drying can be more improved. The adsorption amount is more preferably 2,000 ppm by mass or less, still more preferably 1,000 ppm by mass or less.

The adsorption amount of the cationic surfactant can be controlled by appropriately combining the type of the vinyl monomer (A), the proportion of the constituent unit corresponding to the vinyl monomer (A), and the type of the vinyl monomer (B).

Incidentally, the adsorption amount of the cationic surfactant is, as described in Examples of the present invention, a value measured by the evaluation method based on gas chromatography measurement.

<Production Process of Copolymer>

The copolymer in the cosmetic composition of the present invention can be produced, for example, by mixing monomers giving respective constituent units, or precursors thereof, then copolymerizing the monomers or precursors by solution polymerization, suspension polymerization, emulsion polymerization or other methods, and, if desired, performing addition, condensation reaction or the like of a polysiloxane structure.

The counter ion of the vinyl monomer (A) having a carboxyl group in the structure may be partially or wholly changed to an ion except for hydrogen ion by a neutralization reaction before polymerization and then used for polymerization, or may be partially or wholly changed to an ion except for hydrogen ion by a neutralization reaction after polymerization or other reactions. Such a method can be performed by appropriately selecting it in terms of ease of synthesis.

The polymerization reaction is preferably performed in a hydrophilic solvent. Examples of the hydrophilic solvent include a ketone-based solvent such as acetone, methyl ethyl ketone and methyl isobutyl ketone, an alcohol-based solvent such as methanol, ethanol, n-propanol, i-propanol, n-butanol, i-butanol and sec-butanol, and water. One of these solvents may be used alone, or two or more thereof may be used in combination. Among others, it is preferred to use an alcohol-based solvent.

As the polymerization initiator, for example, an azo compound such as 2,2'-azobisisobutyronitrile, 2,2'-azobis(2,4-dimethylvanitrile), 2,2'-azobis(4-methoxy-2,4-dimethylvaleronitrile), dimethyl-2,2'-azobisisobutyrate, 2,2'-azobis (2-methylbutyronitrile), 1,1'-azobis(1-cyclohexanecarbonitrile), 2,2'-azobis(2-methyl-N-(2-hydroxyethyl)-propionamide and 2,2'-azobis(2-amidinopropane)dihydrochloride, a peroxide such as benzoyl peroxide, dicumyl peroxide, di-tert-butyl peroxide and lauroyl peroxide, a persulfate, or a redox thereof may be used without any particular limitation. The polymerization initiator is preferably used in an amount of 0.01 to 5 mass % based on all monomers.

The polymerization reaction may be performed, for example, in an inert gas atmosphere such as nitrogen or argon, preferably at 30 to 120° C., more preferably at 40 to 100° C., usually for 1 to 30 hours. After the completion of polymerization, the produced copolymer is suitably isolated from the reaction solution by an appropriate technique such as distillation of solvent or addition of poor solvent. This copolymer may be used, directly or after purification, for the production of, for example, a cosmetic preparation. The purification can be performed using reprecipitation, solvent washing, membrane separation or the like, if desired, by appropriately combining these.

2. Cosmetic Composition

The copolymer for use in the present invention can be usefully used as a cosmetic composition by appropriately combining and blending the components described in detail below. In particular, when water, a cationic surfactant and a higher alcohol are mixed under heating, a gel structure called lamella is formed, and this can advantageously give a smooth or moist feel. Furthermore, by blending a silicone oil in the cosmetic composition of the present invention, a dry feel can be imparted.

The cosmetic composition to which the present invention is applied means a composition for an arbitrary cosmetic preparation used for hair and skin and widely includes compositions for so-called cosmetic preparations such as shampoo, rinse, conditioner, treatment, hair dye, perm-setting agent, out-bath treatment, hair pack, hair spray, hair foam, styling agent, body shampoo, makeup cleansing, hand soap, milky lotion, skin lotion, lotion, cream, beauty essence, sunscreen, foundation, lipstick, mascara, eye shadow and depilation agent. The manner of its use may include all of a cosmetic preparation that is applied and well spread on the entirety of skin, hair or the like and then is washed out (rinsed), a cosmetic preparation that is not washed out, and the like.

<Copolymer>

The cosmetic composition of the present invention contains the above-described copolymer as an essential ingredient, and the content of the copolymer is preferably 0.1 mass % or more based on the entire cosmetic composition. Within this range, the adsorption force to skin or hair is increased and a conditioning effect such as smoothness at rinsing or dry feel after drying is obtained. The cosmetic composition of the present invention contains the copolymer more preferably in an amount of 0.2 mass % or more. However, in order to eliminate a stiff feel after drying and increase a moist feel, the content of the copolymer is preferably 5 mass % or less, more preferably 3 mass % or less.

In the cosmetic composition of the present invention, as for the copolymer, only one kind of a copolymer may be used, or two or more kinds of copolymers may be used.

<Water>

In the cosmetic composition of the present invention, a solvent or dispersion medium usable in a cosmetic composition is usually used. The solvent or dispersion medium includes, for example, water and a lower alcohol such as ethanol, isopropanol and butanol, but the cosmetic composition of the present invention contains water.

In the cosmetic composition of the present invention, the content of water is preferably 55 mass % or more based on the entire cosmetic composition. By containing water in an amount of 55 mass % or more, the viscosity can be prevented from becoming excessively high and can be kept at a handleable viscosity, and a good feel upon application can be enhanced. The content of water is more preferably 60 mass % or more. On the other hand, the content of water is preferably 99.6 mass % or less. By containing water in the range above, the cosmetic composition of the present invention can have an appropriate viscous property and be improved in the smoothness upon application and the adsorptivity to skin or hair.

<Cationic Surfactant>

Examples of the cationic surfactant contained in the cosmetic composition of the present invention include an alkyltrimethylammonium salt such as stearyltrimethylammonium chloride and lauryltrimethylammonium chloride, an alkylpyridinium salt such as cetylpyridinium chloride, a distearyldimethylammonium chloride dialkyldimethylammonium salt, a poly(N,N'-dimethyl-3,5-methylenepiperidinium) chloride, an alkyl quaternary ammonium salt, an alkyldimethylbenzylammonium salt, an alkylisoquinolinium salt, a dialkylmorpholinium salt, a polyoxyethylene alkylamine, an alkylamine salt, a polyamine fatty acid derivative, an amyl alcohol fatty acid derivative, a benzalkonium chloride, and a benzethonium chloride.

Only one kind of these cationic surfactants may be used, or two or more kinds thereof may be used in combination.

In the case of using a cationic surfactant, the composition preferably contains the cationic surfactant in a total amount of 20 mass % or less, more preferably 10 mass % or less, based on the entire cosmetic composition. On the other hand, in order to sufficiently impart the function of the cationic surfactant, the composition preferably contains the cationic surfactant in an amount of 0.1 mass % or more, more preferably 1 mass % or more, based on the entire cosmetic composition.

<Higher Alcohol>

The cosmetic composition of the present invention contains a higher alcohol. The "higher alcohol" as used in the description of the present invention means an alcohol having a carbon number of 12 to 24, and a monohydric alcohol is preferred. Specific examples of the higher alcohol include cetyl alcohol and stearyl alcohol.

By using the higher alcohol together with water and the cationic surfactant, a gel called a lamellar structure is formed, and this can impart a smooth or moist feel function to the cosmetic composition. For this reason, the higher alcohol is preferably used together with water and the cationic surfactant. As for the higher alcohol, only one kind of a higher alcohol may be used, or two or more kinds of higher alcohols may be used in combination, but in order to appropriately reduce the viscosity of the cosmetic composition and enhance the smoothness upon application, the composition preferably contains the higher alcohol in a total amount of 20 mass % or less, more preferably 10 mass % or less, based on the entire cosmetic composition. On the other hand, in order to sufficiently impart the function of the higher alcohol, the composition preferably contains the higher alcohol in an amount of 0.1 mass % or more, more preferably 1 mass % or more, based on the entire cosmetic composition, <Silicone Oil>

The cosmetic composition of the present invention contains a silicone oil. The silicone oil for use in the cosmetic composition of the present invention is not particularly limited in its kind, but examples thereof include polydimethylsiloxane, a polydimethylsiloxane alkylene oxide copolymer, an amino-modified polydimethylsiloxane, a polyether-modified polydimethylsiloxane, methylphenylpolysiloxane, an epoxy-modified polydimethylsiloxane, a fluorine-modified polydimethylsiloxane, an alcohol-modified polydimethylsiloxane, an alkyl-modified polydimethylsiloxane, an alkoxy-modified polydimethylsiloxane, and a cyclic silicone. These are described in JP-A-2000-336018.

The polydimethylsiloxane includes those commercially available as "KF96H-1,000,000" (Shin-Etsu Chemical Co., Ltd.), "SH200", "BY11-007", "BY22-029" (all Dow Corning Toray Silicone Co., Ltd.), "TSF451 (Toshiba Silicones), and "L-45" (Nippon Unicar Co., Ltd.).

The polydimethylsiloxane alkylene oxide copolymer includes a copolymer commercially available as "F-178-21" (Nippon Unicar Co., Ltd.).

The amino-modified polydimethylsiloxane includes, for example, those having an aminoalkyl group such as aminoethyl group and aminopropyl group and a propylene glycol-added amino group (modified with aminoglycol), and may have a substituent such as alkyl group and hydroxyl group. The alkyl group is preferably a linear or branched alkyl group having a carbon number of 1 to 12.

The amino-modified polydimethylsiloxane is obtained by copolymerizing dimethylsiloxane with siloxane having the above-described aminoalkyl group, or post-modifying polydimethylsiloxane with a compound having the aminoalkyl group, thereby introducing an aminoalkyl group into the polydimethylsiloxane skeleton. Examples of the commercially available amino-modified polydimethylsiloxane include "USAR SILICONE ALE 56" (Union Carbide Corp.), "ABIL9905" (Goldschmidt AG), "KF857", "KF867", "KF865" (all Shin-Etsu Chemical Co., Ltd.), "SM8702C", "JP8500" (Dow Corning Toray Silicone Co., Ltd.), and "FZ-3707" (Nippon Unicar Co., Ltd.).

The polyether-modified polydimethylsiloxane includes, for example, those having a monomer skeleton such as oxyethylene, oxypropylene, oxybutylene, oxypentamethylene, oxyhexamethylene and oxy(2,2-dimethyl)propylene, and those having an oxyalkylene group of a homopolymer skeleton such as polyoxyethylene, polyoxypropylene, polyoxybutylene, polyoxypentamethylene and polyoxyhexamethylene or of a copolymer skeleton such as polyoxyethylene oxypropylene) copolymer. These may have a substituent such as hydroxyl group and alkyl group. The alkyl group is preferably a linear or branched alkyl group having a carbon number of 1 to 12. Among others, a modified polydimethylsiloxane having an oxyalkylene group in the polymer skeleton is particularly preferred.

Examples of the production method of such a modified polydimethylsiloxane having an oxyalkylene group include a method of copolymerizing dimethylsiloxane with an oxyalkylene group-containing siloxane, and a method of post-modifying polydimethylsiloxane with a compound having the above-described oxyalkylene group, thereby introducing an oxyalkylene group into the polydimethylsiloxane skeleton.

The polyether-modified polydimethylsiloxane is most preferably a modified polydimethylsiloxane obtained by copolymerizing dimethylsiloxane with a siloxane having the above-described oxyalkylene group of a polymer skeleton.

Examples of the commercially available polyether-modified polydimethylsiloxane include "KF945A", "KF351A", "KF354A" (Shin-Etsu Chemical Co., Ltd.), "SH3771C", "SH3749" (Dow Corning Toray Silicone Co., Ltd.), "L-7602C", "L-720" (Nippon Unicar Co., Ltd.), and "SF1066" (General Electrics Company).

As the methylphenylpolysiloxane, for example, "KF56" (Shin-Etsu Chemical Co., Ltd.), "SH5" (Shin-Etsu Chemical Co., Ltd.), "PS922" (Chisso Corp.), and "L-930" (Nippon Unicar Co., Ltd.) are commercially available.

As the fluorine-modified polydimethylsiloxane, for example, "X-22-820" (Shin-Etsu Chemical Co., Ltd.) and "PS182" (Chisso Corp.) are commercially available.

As the alcohol-modified polydimethylsiloxane, for example, "KF851" (Shin-Etsu Chemical Co., Ltd.), "FM4411" (Chisso Corp.), "FZ-3722" and "F-235-21" (Nippon Unicar Co., Ltd.) are commercially available.

As the alkyl-modified polydimethylsiloxane, for example, "KF410", "KF-413" (Shin-Etsu Chemical Co., Ltd.), "PS130" and "PS137" (Chisso Corp.) are commercially available.

As the alkoxy-modified polydimethylsiloxane, for example, "PS912" (Chisso Corp.) and "FZ-3701" (Nippon Unicar Co., Ltd.) are commercially available.

As the cyclic silicone, for example, "SH244", "SH245" and "SH246" (Dow Corning Toray Silicone Co., Ltd.) are commercially available, One kind of a silicone oil may be used alone, or two or more kinds of silicone oils may be used in combination. If the blending amount of the silicone oil is excessively large, a heavy feel remains after applying the composition to hair and drying it. Therefore, the composition preferably contains the silicone oil in a total amount of 10 mass % or less, more preferably 8 mass % or less, based on the entire cosmetic composition. On the other hand, in order to sufficiently impart the function of the silicone oil, the composition preferably contains the silicone oil in an amount of 0.1 mass % or more, more preferably 1 mass % or more, based on the entire cosmetic composition.

<Other Components>

In addition to the above-described copolymer, water, cationic surfactant, higher alcohol and silicone oil, for example, a hydrocarbon oil, a humectant (water-soluble polymer) a copolymer such as cationic polymer, anionic polymer, non-ionic polymer and amphoteric polymer, various surfactants other than the cationic surfactant, a pH adjusting agent, an antiseptic, and a thickener may be used in appropriate combination as long as the effects of the cosmetic composition of the present invention are not impaired.

Examples of the hydrocarbon oil include a liquid paraffin such as isoparaffin, a solid paraffin, vaseline, ceresin, and microcrystalline wax. Only one kind of these hydrocarbon oils may be used, or two or more kinds thereof may be used in combination. The composition preferably contain the hydrocarbon oil in a total amount of 5 mass % or less based on the entire cosmetic composition.

Examples of the humectant include a polyhydric alcohol such as glycerin, dipropylene glycol, 1,3-butanediol and erythritol, and a water-soluble polymer such as methylcellulose and hyaluronic acid. Examples of the cationic polymer include a cation-modified cellulose ether derivative, a cation-modified galactomannan polysaccharide, a polydimethyldiallylammonium halide, and a copolymer of a dimethyldiallylammonium halide and an acrylamide. Examples of the anionic polymer include an acrylic acid derivative (such as polyacrylic acid or its salt, acrylic acid.acrylamide.ethyl acrylate polymer or its salt, and acrylic acid/acrylic acid alkyl ester/steareth-20 methacrylate polymer or its salt), a methacrylic acid derivative, and a crotonic acid derivative; examples of the nonionic polymer include an acrylic acid derivative (such as hydroxyethyl acrylate.methoxyethyl acrylate polymer and polyacrylamide), and a vinylpyrrolidone derivative (such as polyvinylpyrrolidone and vinylpyrrolidone.vinyl acetate polymer); and examples of the amphoteric polymer include dimethyldiallylammonium chloride derivative (such as acrylamide.acrylic acid. dimethyldiallylammonium chloride polymer and acrylic acid.dimethyldiallylammonium chloride polymer). In the case of using such a polymer, the composition preferably contains the polymer in a total amount of 5 mass % or less based on the entire cosmetic composition.

Examples of the surfactant other than the cationic surfactant include an anionic surfactant, a hydrophilic nonionic surfactant, an amphoteric surfactant, and a semipolar surfactant. Specific examples of the surfactant other than the cationic surfactant are described below, and in the case of using such a surfactant, the composition preferably contains the surfactant in a total amount of 5 mass % or less based on the entire cosmetic composition.

As the anionic surfactant, there may be used an anionic surfactant usually used in a normal cosmetic composition, such as α-olefin sulfonate, a higher alcohol sulfuric acid ester salt, a polyoxyethylene alkyl ether sulfuric acid ester salt, a paraffin sulfonate, a polyoxyethylene alkyl ether carboxylic ester salt, an alkylsulfosuccinate, an N-acyl-β-alanine salt, an N-acyl glutamate and acylmethyl taurine salt. Examples of the counter ion of such an anionic surfactant include sodium, potassium, ammonium, triethanolamine, and diethanolamine.

Examples of the hydrophilic nonionic surfactant include polyoxyethylene (hereinafter sometimes referred to as POE) sorbitan fatty acid esters (such as POE sorbitan monooleate, POE sorbitan monostearate, POE sorbitan monooleate and POE sorbitan tetraoleate); POE sorbitol fatty acid esters (such as POE sorbitol monolaurate, POE sorbitol monooleate, POE sorbitol pentaoleate and POE sorbitol monostearate); POE glycerol fatty acid esters (such as POE monooleate, e.g., POE glycerol monostearate, POE glycerol monoisostearate, POE glycerol triisostearate); POE fatty acid esters (such as POE distearate, POE monodioleate and ethylene glycol distearate); POE alkyl ethers (such as POE lauryl ether, POE oleyl ether, POE stearyl ether, POE behenyl ether, POE 2-octyldodecyl ether and POE cholestanol ether); pluronic types (such as pluronic); POE.polyoxypropylene (hereinafter sometimes referred to as POP) alkyl ethers (such as POE.POP cetyl ether, POE.POP-2-decyltetradecyl ether, POE.POP monobutyl ether, POE.POP hydrogenated lanolin and POE-.POP glycerol ether); tetra-POE.tetra-POP ethylenediamine condensates (such as tetronic); POE caster oil-hydrogenated caster oil derivatives (such as POE caster oil, POE hydrogenated caster oil, POE hydrogenated caster oil monoisostearate, POE hydrogenated caster oil triisostearate, POE hydrogenated caster oil monopyroglutarnic acid monoisostearic acid diester and POE hydrogenated caster oil maleic acid); POE bees wax.lanolin derivatives (such as POE sorbitol bees wax); an alkanolamide (such as coconut oil fatty acid diethanolamide, lauric acid monoethanolamide and fatty acid isopropanolamide); a POE propylene glycol fatty acid ester; a POE alkylamine; a POE fatty acid amide; a sucrose fatty acid ester; an alkylethoxydimethylamine oxide; and a trioleylphosphoric acid.

Examples of the amphoteric surfactant include an imidazoline-based amphoteric surfactant such as 2-undecyl-N,N,N-(hydroxyethylcarboxymethyl)-2-imidazoline sodium and 2-cocoyl-2-imidazolinium hydroxide-1-carboxyethyloxy disodium salt; and a betaine-based surfactant such as 2-heptadecyl-N-carboxymethyl-N-hydroxyethylimidazolinium betaine, lauryldimethylaminoacetic acid betaine, alkylbetaine, amidobetaine and sulfobetaine.

Examples of the semipolar surfactant include lauramine oxide (lauryldimethylamine oxide), and this can be suitably used.

These surfactants are generally available on the market, and the commercially available surfactant may be used as it is.

Examples of the pH adjusting agent include a citric acid and a tartaric acid. In the case of using a pH adjusting agent, the content thereof is preferably 0.1 mass % or less based on the entire cosmetic composition.

Examples of the antiseptic include sodium benzoate. In the case of using an antiseptic, the content thereof is preferably 0.1 mass % or less based on the entire cosmetic composition.

Examples of the thickener include hydroxymethyl cellulose and hydroxyethyl cellulose. In the case of using a thickener, the content thereof is preferably 5 mass % or less based on the entire cosmetic composition.

In addition to those described above, a natural extract from animal and plant or its derivative, an organic acid such as lactic acid, an inorganic salt such as sodium chloride, amino acids (such as glutamic acid or its salt, arginine or its salt, and glycine), an antioxidant, an ultraviolet absorber, a fungicide, a chelating agent, a flagrance, a coloring agent, a sequestering agent (such as edetate), a foaming promoter, and the like may appropriately blended as long as the effects of the present invention are not impaired. In the case of using such an ingredient, the composition preferably contains the ingredient in a total amount of 20 mass % or less based on the entire cosmetic composition.

Incidentally, the cosmetic composition of the present invention is not precluded from using an ingredient other than those descried above.

The viscosity of the cosmetic composition of the present invention varies depending on its usage but, for example, in the case of using the cosmetic composition of the present invention as a hair cosmetic, the viscosity at 25° C. is preferably from 3,000 to 100,000 mPa·s. This viscosity is more preferably 4,000 mPa·s or more, still more preferably 5,000 mPa·s or more, and on the other hand, more preferably 90,000 mPa·s or less, still more preferably 80,000 mPa·s or less. When the viscosity of the cosmetic composition is from 3,000 to 100,000 mPa·s, this is preferred in view of handling. As described in Examples in the description of the present invention, the viscosity of the cosmetic composition can be measured using a B-type viscometer or a B8H-type viscometer.

3. Hair Cosmetic

The cosmetic composition is useful particularly as a hair cosmetic. The "hair cosmetic" as used in the description of the present invention is not particularly limited, but examples thereof include a shampoo, a rinse, a conditioner, a treatment, an out-bath treatment, a hair dye, a perm-setting agent, a hair pack, a hair spray, a hair foam, and a styling agent. Among these, the hair cosmetic of the present invention is useful as a conditioning agent requiring a conditioning effect, such as shampoo, rinse, conditioner, treatment and out-bath treatment.

4. Hair Treatment Cosmetic

Among hair cosmetics, the cosmetic composition of the present invention is useful particularly as a hair treatment cosmetic. The "hair treatment cosmetic" is primarily intended to impart a conditioning effect after washing with a shampoo or the like and includes a cosmetic preparation that is washed out with water after application to hair, and a cosmetic preparation that is not washed out after application. The cosmetic preparation that is washed out includes a cosmetic preparation also called a rinse-off conditioner, such as rinse, conditioner and treatment, and the cosmetic preparation that is not washed out includes a cosmetic preparation called an out-bath treatment, a leave-on conditioner and the like. Among others, the cosmetic composition is useful as a rinse-off conditioner.

EXAMPLES

The present invention is described in greater detail below by referring to Examples, but the present invention is not limited to these Examples as long as its purport is observed.

[Production of Copolymer]
<Production of Copolymer (1)>

100 Parts by mass of ethanol was charged into a reaction vessel equipped with a reflux condenser, a dropping funnel, a thermometer, a nitrogen gas inlet tube and a stirring device, and a monomer mixture solution containing 70 parts by mass of methoxypolyethylene glycol (4 mol) methacrylate, 30 parts by mass of acrylic acid and 100 parts by mass of ethanol was charged into the dropping funnel. The reaction vessel was purged with nitrogen and then heated to 80° C. Subsequently, 0.5 parts by mass of dimethyl-2,2'-azobisisobutyrate (V-601, produced by Wako Pure Chemical Industries, Ltd.) was charged into the reaction vessel and then, the monomer mixture solution was added dropwise thereto over 2 hours. After the completion of dropwise addition, the reaction was allowed to proceed for 8 hours, and the resulting reaction solution was cooled to obtain Copolymer (1).

<Production of Copolymer (2) to Copolymer (9)>

Copolymer (2) to Copolymer (9) were produced in the same manner as in the production of Copolymer (1) except for using the monomers shown in Table-1 in the ratio shown in Table-1,

[Measurement of Physical Properties of Copolymer]
<Measurement of Weight Average Molecular Weight>

The weight average molecular weight of each of Copolymers (1) to (9) was determined by gel permeation chromatography (apparatus: "SC8010, SD8022, RI8020, CO8011, PS8010" manufactured by Tosoh Corporation, column: "Wakopak (Wakobeads G-50)" manufactured by Wako Pure Chemical Industries, Ltd., developing solvent: water/methanol/acetic acid/sodium acetate=6/4/0.3/0.41) using polyethylene glycol as a standard substance. The results obtained are shown in Table-1.

[Preparation of Chemical Composition]

Using Copolymers (1) to (9), cosmetic compositions according to the formulations shown in Table-2 were prepared in a usual way. However, in Comparative Example 6, the cosmetic composition was prepared in the same manner as in Example 1 except that out of the cosmetic composition according to the formulation shown in Table-2, a higher alcohol was not blended.

[Measurement of Physical Properties and Evaluation of Cosmetic Composition]
<Measurement of Adsorption Amount of Cationic Surfactant>

Human black hair (100%) bundled at the root (untreated hair: 10 g×30 cm, produced by Beaulax) was used as the hair bundle for evaluation, and the hair after subjecting the hair bundle to a bleach treatment was used as "damaged hair". That is, a bleach obtained by mixing 12 g of "Promatiz Flaeve Oxytan 6.0 (6% hydrogen peroxide cream)" produced by Milbon Co., Ltd. and 6 g of "Powder Bleach MR2" produced by Meros Chemical Company was applied to one hair bundle, left standing for 30 minutes, washed with water and then washed with sodium lauroyl (EO)3 sulfate (polyoxyethylene (3) lauroyl ether sodium sulfate) to prepare a damaged hair. A damaged hair sample bundle was obtained by bundling 5 g of the damaged hair.

The damaged hair sample bundle was washed/rinsed by using 25 mass % polyoxyethylene (3) lauryl ether sodium sulfate as the shampoo and then, 0.5 g of each of the cosmetic composition samples above was applied thereto and rinsed by combing the hair 20 times in running water. Thereafter, the hair was immersed in isopropyl alcohol and subjected to an ultrasonic treatment for 1 hour to extract the adsorbed cationic surfactant. The adsorption amount of the cationic surfactant was determined by performing the quantitative analysis by gas chromatography ("HP6850C-R5A", manufactured by, Hewlett-Packard Co.).

<Evaluation of Smoothness Upon Application>

The damaged hair sample bundle prepared above was washed/rinsed by using 25 mass % polyoxyethylene (3) lauryl ether sodium sulfate as the shampoo and after applying each of the hair cosmetic compositions above thereto, smoothness in finger combing at the time of rinsing the hair bundle in running water at 40° C. was rated on the following 4-point scale. Incidentally, the reference standard product indicates the cosmetic composition prepared above by not blending the copolymer.

4: Excellent as compared with the reference standard product.
3: Equal to the reference standard product.
2: Slightly inferior to the reference standard product.
1: Inferior to the reference standard product.

<Measurement of Viscosity>

The cosmetic composition prepared was measured for the viscosity at 25° C. by using a B-type viscometer (Examples 1 to 4 and Comparative Examples 2 to 6) or a B8H-type viscometer (Comparative Example 1). Here, the rotor No. and the rotation speed used in the viscosity measurement were as shown in Table-3.

TABLE 1

Kind and proportion (parts by mass) of monomer used for production of copolymer and weight average molecular weight of copolymer

|  |  | Copolymer (1) | Copolymer (2) | Copolymer (3) | Copolymer (4) | Copolymer (5) | Copolymer (6) | Copolymer (7) | Copolymer (8) | Copolymer (9) |
|---|---|---|---|---|---|---|---|---|---|---|
| Vinyl monomer (A) | Acrylic acid | 30 | 30 | 30 | 30 | 10 | 30 | 30 | 30 | 30 |
| Vinyl monomer (B) | methoxy PEG (4 mol) methacrylate* | 70 | 60 | 50 | 50 | 70 |  |  |  |  |
| Vinyl monomer (C) | Isostearyl acrylate |  | 10 | 20 |  |  |  |  |  |  |
|  | Stearyl methacrylate |  |  |  |  |  | 20 |  |  |  |
|  | Synthetic lauryl methacrylate |  |  |  | 20 |  |  |  |  |  |
| Other vinyl monomers | Glycerol methacrylate |  |  |  |  |  |  | 70 |  |  |
|  | Hydroxyethyl methacrylate |  |  |  |  |  |  |  | 70 |  |
|  | Hydroxyethylacrylamide |  |  |  |  |  |  |  |  | 70 |

TABLE 1-continued

Kind and proportion (parts by mass) of monomer used for production of copolymer and weight average molecular weight of copolymer

| | Copolymer (1) | Copolymer (2) | Copolymer (3) | Copolymer (4) | Copolymer (5) | Copolymer (6) | Copolymer (7) | Copolymer (8) | Copolymer (9) |
|---|---|---|---|---|---|---|---|---|---|
| Methoxy PEG (23 mol) methacrylate* | | | | | | | | | 70 |
| Weight average molecular weight | 24000 | 27000 | 25000 | | 54000 | | | 22000 | 14000 |

In Table-1, the blank in the vinyl monomer indicates that the vinyl monomer was not used.
In Table-1, the blank in the weight average molecular weight indicates that the weight average molecular weight was not measured.
*Methoxy PEG (n mol) methacrylate is a methacrylate of methoxy polyethylene glycol (n mol), and n indicates r = n in formula (1).
Methoxy PEG (4 mol) methacrylate*: "NK Ester N40G" produced by Shin-Nakamura Chemical Co., Ltd.
Isostearyl acrylate: "NK Ester S1800A" produced by Shin-Nakamura Chemical Co., Ltd.
Stearyl methacrylate: "AcrylEster SMA" produced by Mitsubishi Rayon Co., Ltd.
Synthetic lauryl methacrylate: "AcrylEster SLMA" produced by Mitsubishi Rayon Co., Ltd.
Glycerol methacrylate: "BLEMMER GLM" produced by NOF Corp.
Hydroxyethyl methacrylate: "Hydroxyethyl Methacrylate" produced by Wako Pure Chemical Industries, Ltd.
Hydroxyethylacrylamide: "HEAA" produced by Kohjin Co., Ltd.
Methoxy PEG (23 mol) methacrylate*: "NK Ester N230G" produced by Shin-Nakamura Chemical Co., Ltd.

TABLE 2

Blending formulation of cosmetic composition (mass %)

| | | |
|---|---|---|
| | Any one of Copolymers (1) to (9) | 1 |
| Cationic surfactant | Stearyltrimethylammonium chloride | 1.5 |
| Higher alcohol | Cetyl alcohol | 2 |
| | Stearyl alcohol | 3 |
| Silicone Oil | Polydimethylsiloxane | 1.5 |
| | Aminoglycol-modified polydimethylsiloxane | 0.5 |
| Hydrocarbon Oil | Isoparaffin | 2 |
| Thickener | Hydroxyethyl cellulose | 1 |
| Humectant | Glycerin | 5 |
| pH Adjusting agent | Citric acid | 0.02 |
| Antiseptic | Sodium benzoate | 0.2 |
| | Water | balance |

Stearyltrimethylammonium chloride: produced by Wako Pure Chemical Industries, Ltd.
Cetyl alcohol: produced by Wako Pure Chemical Industries, Ltd.
Stearyl alcohol: produced by Wako Pure Chemical Industries, Ltd.
Polydimethylsiloxane: "SH200" produced by Dow Corning Toray Silicone Co., Ltd.
Aminoglycol-modified polydimethylsiloxane: "JP8500" produced by Dow Corning Toray Silicone Co., Ltd.
Isoparaffin: "IP2028" produced by Idemitsu Kosan Co., Ltd.
Hydroxyethyl cellulose: "Natrosol 250HR" produced by Hercules
Glycerin: "JP Glycerin" produced by Tokai Seiyaku

TABLE 3

Evaluation of Cosmetic Composition

| | Example 1 | Example 2 | Example 3 | Example 4 | Comparative Example 1 |
|---|---|---|---|---|---|
| Copolymer blended | Copolymer (1) | Copolymer (2) | Copolymer (3) | Copolymer (4) | Copolymer (5) |
| Higher alcohol | blended | blended | blended | blended | blended |
| Adsorption amount of cationic surfactant (ppm by mass) | 233 | 302 | 173 | 177 | 44 |
| Smoothness upon application | 3 | 4 | 4 | 3 | 3 |
| Viscosity (mPa · s) | 6990 | 25500 | 13000 | 25250 | 39800 |
| Viscosity measurement conditions  Rotation speed (rpm) | 12 | 6 | 12 | 12 | 5 |
| Rotor No. | #3 | #4 | #4 | #3 | #6 (*) |

| | Comparative Example 2 | Comparative Example 3 | Comparative Example 4 | Comparative Example 5 | Comparative Example 6 |
|---|---|---|---|---|---|
| Copolymer blended | Copolymer (6) | Copolymer (7) | Copolymer (8) | Copolymer (9) | Copolymer (1) |
| Higher alcohol | blended | blended | blended | blended | none |
| Adsorption amount of cationic surfactant (ppm by mass) | 222 | 332 | 240 | 35 | 168 |
| Smoothness upon application | 1 | 1 | 2 | 3 | 1 |
| Viscosity (mPa · s) | 1050 | 2750 | 1300 | 72000 | 17 |
| Viscosity measurement conditions  Rotation speed (rpm) | 12 | 12 | 12 | 6 | 60 |
| Rotor No. | #3 | #3 | #3 | #4 | #2 |

(*): A B8H-type viscometer was used.

[Evaluation of Results]

(1) The cosmetic compositions of Examples 1 to 4 exhibited a high adsorption amount of the cationic surfactant without impairing the smoothness upon application.

(2) With respect to the cosmetic composition of Comparative Example 1 where the blending amount of the vinyl monomer (A) was 10 mass % and smaller than the scope of the present invention, the smoothness upon application was equal to the reference standard product but the adsorption amount of the cationic surfactant was small.

(3) With respect to the cosmetic compositions of Comparative Examples 2 to 4 where r in formula (1) representing the vinyl monomer (B) was 1 and the side chain length was shorter than in the vinyl monomer (B) specified by the present invention, in all cases, the adsorption amount of the cationic surfactant was large but the smoothness upon application was poor.

(4) With respect to the cosmetic composition of Comparative Example 5 where r in formula (1) representing the vinyl monomer (B) was 23 and the side chain length was longer than in the vinyl monomer (B) specified by the present invention, the smoothness upon application was equal to the reference standard product but the adsorption amount of the cationic surfactant was small.

(5) With respect to the cosmetic composition of Comparative Example 6 which was a composition not containing a higher alcohol, the adsorption amount of the cationic surfactant was high but due to low viscosity, the smoothness upon application was poor.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2010-237635) filed on Oct. 22, 2010 and Japanese Patent Application (Patent Application No. 2011-212630) filed on Sep. 28, 2011, the contents of which are incorporated herein by reference.

Industrial Applicability

The cosmetic composition of the present invention can provide an excellent conditioning effect particularly when used as a hair cosmetic.

The invention claimed is:

1. A cosmetic composition, comprising:
a copolymer having a constituent unit corresponding to (A) a vinyl monomer having a carboxyl group in a structure and a constituent unit corresponding to (B) a vinyl monomer represented by the following formula (1);
a cationic surfactant;
a higher alcohol; and
a silicone oil;

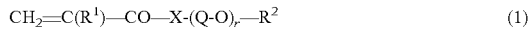

$$CH_2=C(R^1)-CO-X-(Q-O)_r-R^2 \qquad (1)$$

wherein in formula (1), $R^1$ represents a hydrogen atom or a methyl group; $R^2$ represents a hydrogen atom or an alkyl group having a carbon number of 1 to 5, each of which may have a substituent; Q represents an alkylene group having a carbon number of 2 to 4, which may have a substituent; r represents an integer of 2 to 15; and X represents an oxygen atom or NH, provided that in formula (1), the number of atoms bonded linearly to each other in the structure of $-(Q-O)_r-R^2$ is 70 or less, and
wherein a proportion of the constituent unit corresponding to the vinyl monomer (A) is from 15 to 60 mass % based on the total mass of the copolymer.

2. The cosmetic composition according to claim 1, wherein a proportion of the constituent unit corresponding to the vinyl monomer (B) is from 40 to 85 mass % based on the total mass of the copolymer.

3. The cosmetic composition according to claim 1, wherein the vinyl monomer (A) is represented by the following formula (2) or (3):

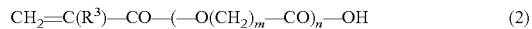

$$CH_2=C(R^3)-CO-(-O(CH_2)_m-CO)_n-OH \qquad (2)$$

wherein in formula (2), $R^3$ represents a hydrogen atom or a methyl group; m represents an integer of 1 to 4; and n represents an integer of 0 to 4:

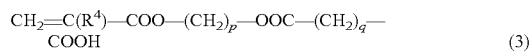

$$CH_2=C(R^4)-COO-(CH_2)_p-OOC-(CH_2)_q-COOH \qquad (3)$$

wherein in formula (3), $R^4$ represents a hydrogen atom or a methyl group; and each of p and q independently represents an integer of 2 to 6.

4. The cosmetic composition according to claim 1, wherein a weight average molecular weight of the copolymer is from 3,000 to 2,000,000.

5. The cosmetic composition according to claim 1, wherein the copolymer further contains a constituent unit corresponding to (C) a vinyl monomer having an alkyl group with a carbon number of 12 to 22 in an amount of 40 mass % or less based on the total mass of the copolymer.

6. The cosmetic composition according to claim 1, which comprises:
from 0.1 to 5 mass % of the copolymer; and
from 55 to 99.6 mass % of water.

7. The cosmetic composition according to claim 1, which comprises:
from 0.1 to 20 mass % of the cationic surfactant.

8. The cosmetic composition according to claim 1, which comprises: from 0.1 to 20 mass % of the higher alcohol.

9. The cosmetic composition according to claim 1, which comprises: from 0.1 to 10 mass % of the silicone oil.

10. A hair cosmetic, comprising:
the cosmetic composition according to claim 1.

11. A hair treatment cosmetic, comprising:
the cosmetic composition according to claim 1.

* * * * *